United States Patent [19]

Johnsen et al.

[11] Patent Number: 5,026,360
[45] Date of Patent: Jun. 25, 1991

[54] CLAMPING SYSTEMS FOR TWO PIECE OSTOMY DEVICE

[75] Inventors: Kenneth A. Johnsen, Piscataway, N.J.; Walter F. Leise, Jr., Yardley, Pa.

[73] Assignee: E. R. Squibb & Sons, Princeton, N.J.

[21] Appl. No.: 585,021

[22] Filed: Sep. 18, 1990

Related U.S. Application Data

[62] Division of Ser. No. 372,439, Jun. 27, 1989, abandoned.

[51] Int. Cl.⁵ .............................................. A61F 5/44
[52] U.S. Cl. ..................................... 604/338; 604/339
[58] Field of Search ............... 604/332, 338, 339, 342, 604/343

[56] References Cited

U.S. PATENT DOCUMENTS

| | | | |
|---|---|---|---|
| 1,518,479 | 12/1924 | Brewer | 285/409 |
| 3,042,430 | 8/1958 | Guy | 285/365 |
| 3,276,089 | 10/1966 | Cheever et al. | 285/409 |
| 3,789,846 | 2/1974 | Barrett et al. | 604/343 |
| 4,438,958 | 3/1984 | DeCenzo | 285/409 |
| 4,963,136 | 10/1990 | Steer et al. | 604/339 |

FOREIGN PATENT DOCUMENTS 679429  2/1964  Canada ................................ 604/343

OTHER PUBLICATIONS

United Surgical Corporation, Ostomy Catalog, 1968, p. 21.

*Primary Examiner*—Ronald Frinks
*Assistant Examiner*—R. Clarke
*Attorney, Agent, or Firm*—James & Franklin

[57] ABSTRACT

To minimize trauma after surgery, a clamp is employed to sealingly engage specially configured coupling rings mounted on the adhesive faceplate and the collection pouch, respectively. Each of the coupling rings includes a radially extending annular projection. The circular clamp is designed to surround the coupling rings and receive the projections within an annular recess. The projections and recess have oppositely oriented camming surfaces which cooperates to draw the coupling rings toward each other as the clamp is tightened. The clamp is locked by a toggle clasp connected by a living hinge, a pin and socket arrangement, a serrated clasp or a change purse type clasp. An adaptor can be employed so that the clamp can be used with a pouch with a conventionally configured coupling ring.

23 Claims, 9 Drawing Sheets

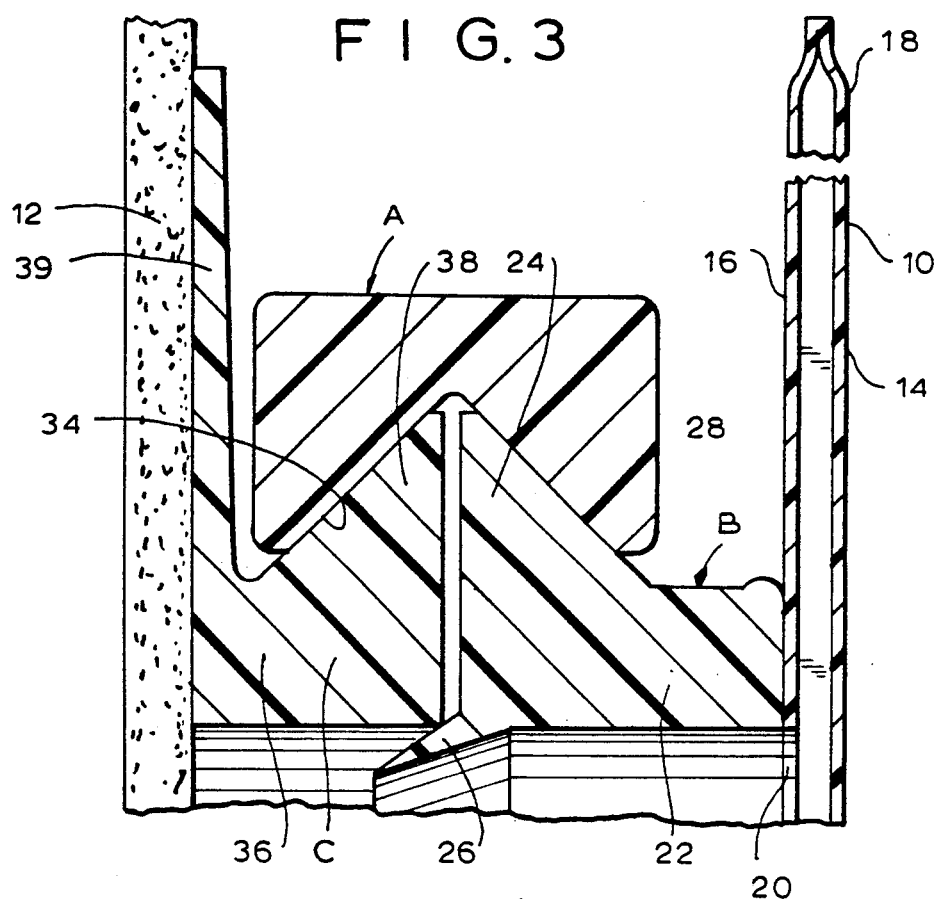

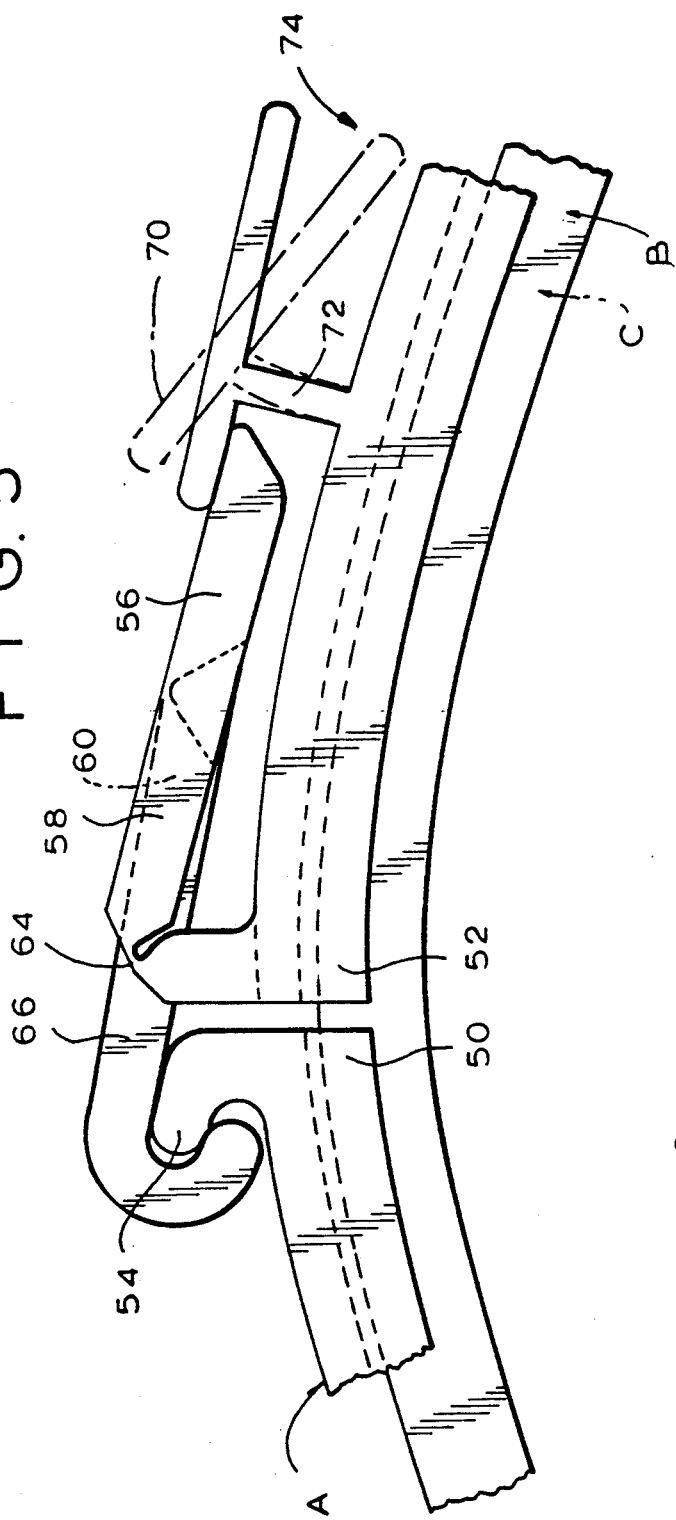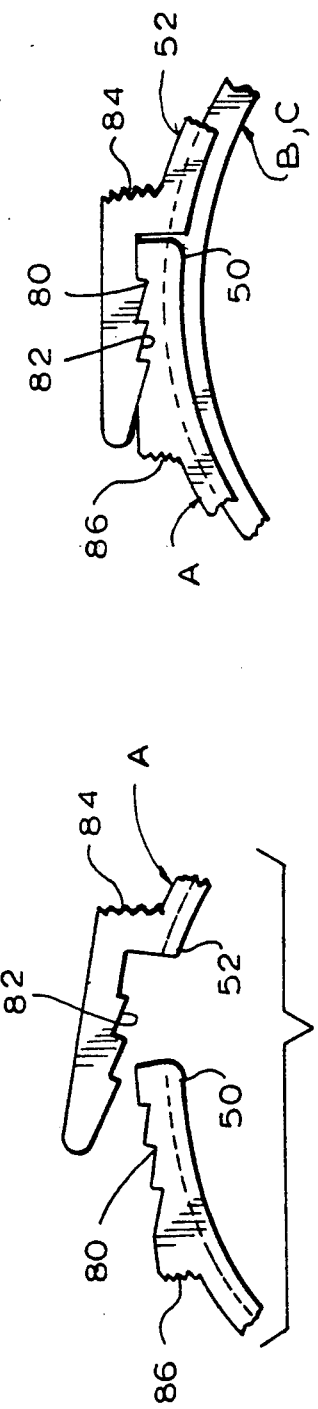

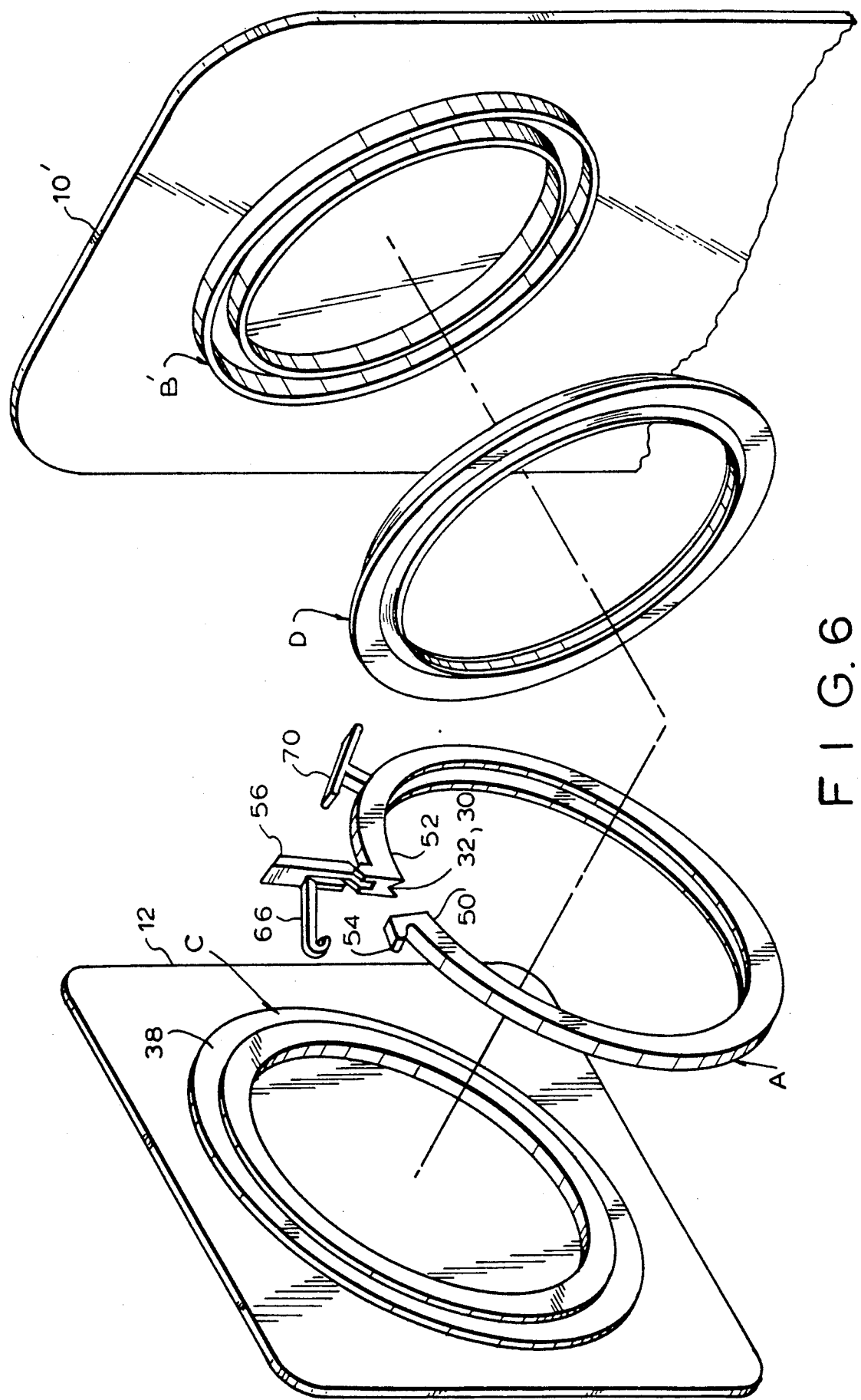

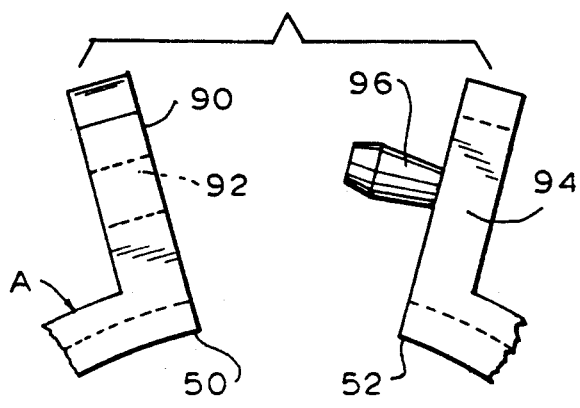
FIG. 11
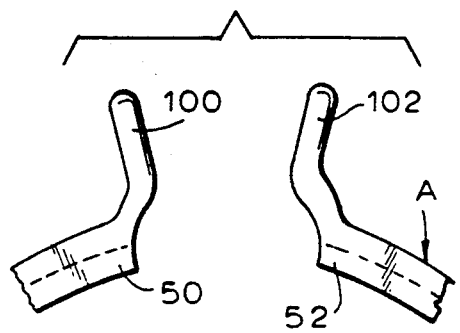
FIG. 15
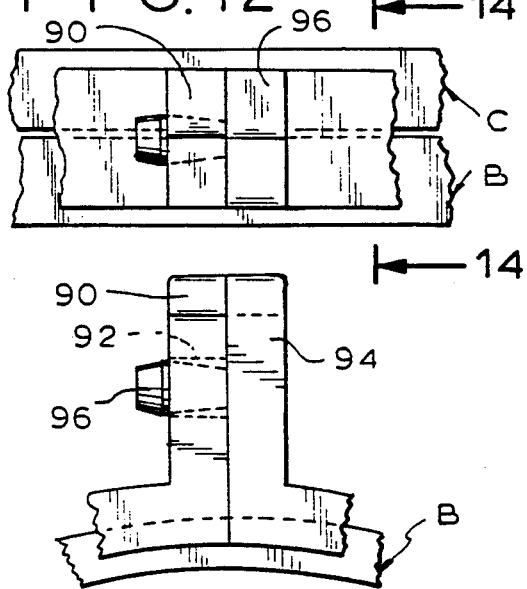
FIG. 12
FIG. 13
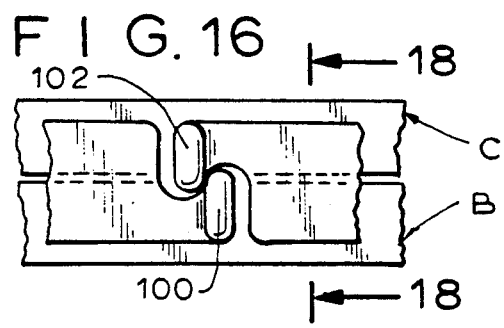
FIG. 16
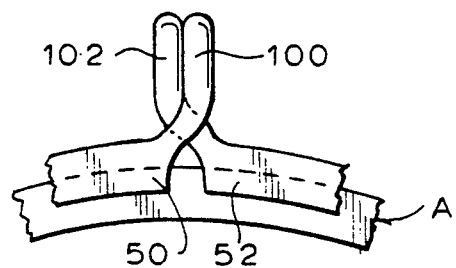
FIG. 17
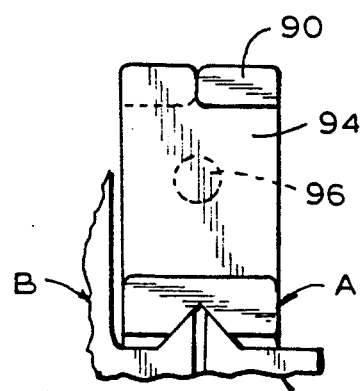
FIG. 14
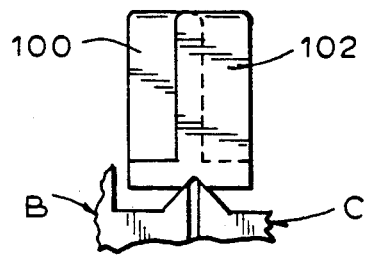
FIG. 18

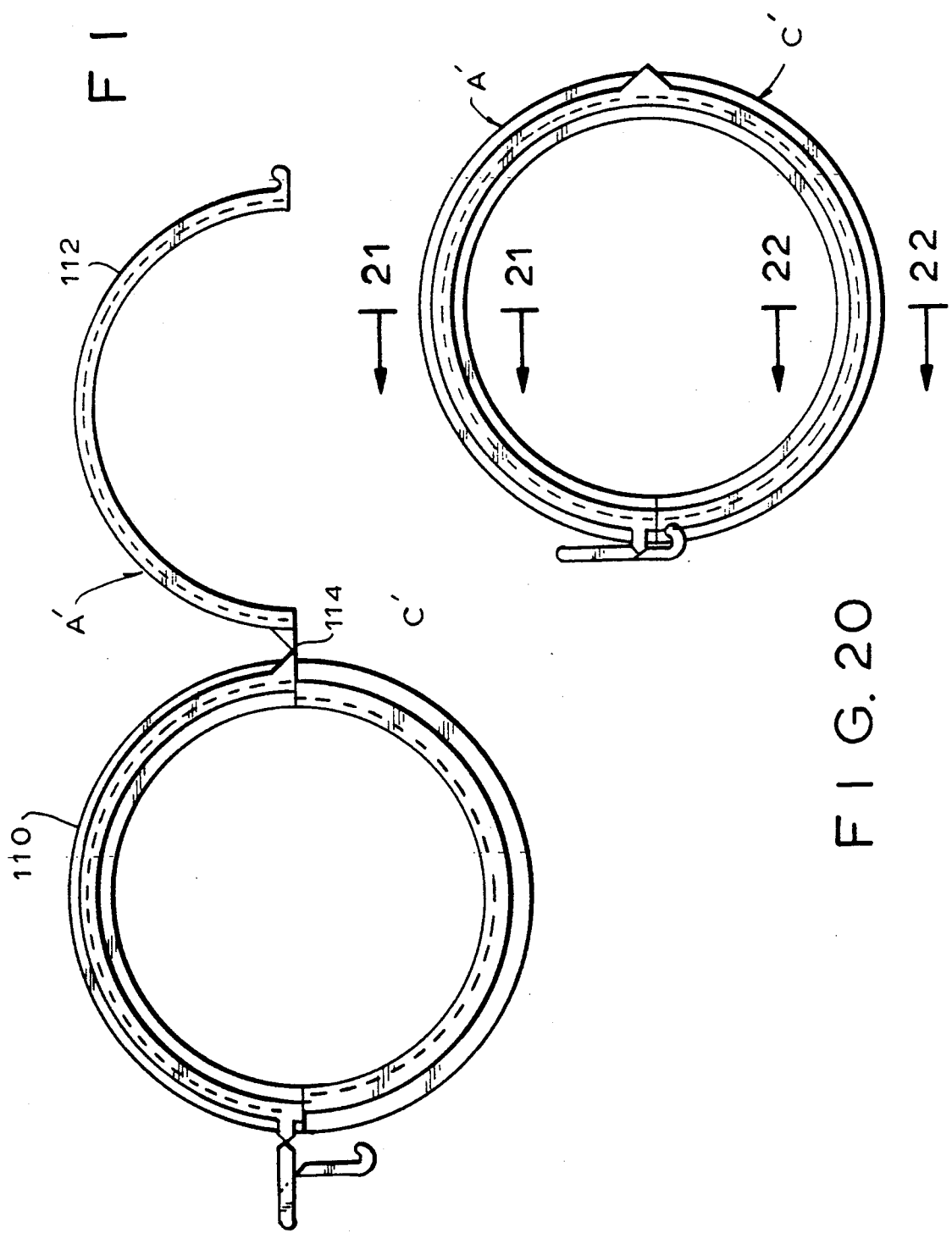

CLAMPING SYSTEMS FOR TWO PIECE OSTOMY DEVICE

This is a divisional of co-pending application Ser. No. 372,439 filed on June 27, 1989 now abandoned.

The present invention relates to ostomy devices and more particularly to a system for clamping specially configured coupling rings of a two piece ostomy appliance to permit trauma free mounting and removal of the pouch.

Abdominal surgery such as colostomy, ileostomy and urostomy often results in an opening or stoma in the abdominal wall through which waste is discharged. Because the patient has no control over the discharge, an ostomy device is affixed to the body to collect the discharge and protect the stoma. The device includes a waste collection pouch or bag affixed to the skin surrounding the stoma.

Although the present invention is disclosed in the context of an ostomy device, its use is not limited to ostomy appliance. Other medical techniques such as wound care and irrigation may require the attachment of pouches, bags or other types of collection receptacles under conditions which do not permit the application of any force to the patient. The present invention may be applicable in those situations as well.

In one popular form, an ostomy device includes a collection pouch which is mounted to the skin of the patient by means of an adhesive flexible member called a faceplate or dressing. The faceplate has an opening through which the stoma may extend.

Ostomy devices of this type are commercially available in one piece and two piece constructions. In the one piece type, the collection pouch is permanently affixed to the faceplate. When the pouch is full of waste, the entire device must be removed and replaced. Because it may be irritating and discomforting to the patient to have the adhesive backed faceplate removed and replaced, the two piece system was developed. This type permits the pouch to be detached from the faceplate such that the faceplate does not have to be removed each time the pouch is changed.

U.S. Pat. No. 4,460,363 to Steer et al, issued July 17, 1984 and entitled OSTOMY BAG, describes one such two piece ostomy system which has been commercially successful. That patent discloses a system in which the ostomy bag is securely coupled to an adhesive faceplate or dressing which is affixed to the skin around the stoma. The bag can be removed without disturbing the dressing. The system involves a first coupling member bonded to the faceplate and a second second coupling member bonded to the ostomy bag around the stoma opening. One of the coupling members consists of an upstanding rib or other projection which is dimensioned to be sealingly engaged within a channel in the other coupling member as the members are snapped together.

While the above described two piece system has been commercially successful, it is recogized that for certain applications the coupling system could be improved. In order to snap the coupling members together, it is necessary to exert a force which is directed towards the body of the patient. This force is applied to the patient's body in the area surrounding the stoma. Since the area surrounding the stoma may be irritated and sensitive, particularly shortly after surgery, the application of any force in this area is contraindicated.

To reduce the problem of the application of force on the tender area surrounding the stoma as the pouch is mounted or removed, the Steer ostomy device has been modified by mounting the coupling member to the surface of the faceplate such that the fingers can be inserted behind the coupling member to absorb the coupling force. This mounting construction employs an accordion type member which can be expanded when necessary to form a recess into which the fingers may be received. It is described in detail in co-pending application Ser. No. 503,754, filed June 13, 1983 in the name of Ole Jensen and entitled IMPROVED OSTOMY DEVICE. Another modification shown in U.S. Pat. No. 4,419,100 of Alexander employs a resilient web between the body side coupling member and the adhesive faceplate to allow for a limited floating action.

While the accordian modification is quite effective in reducing the amount of force applied to the body when snapping the coupling members together, it does not eliminate the force entirely, as a small amount of force is still applied to the body during the process of expanding the accordion fold. There are, however, certain instances in which it is necessary to eliminate the force altogether, notably in the operating room or immediately thereafter. In order to minimize trauma during these critical times, we have devised a system of connecting and sealing the coupling members in a manner in which absolutely no force is exerted on the patient's body. In general, this objective is achieved through the use of a circular clamp adapted to surround and sealingly connect specially configured coupling members. The clamp is affixed by applying a force directed only radially with respect to the coupling members and hence only parallel to patient's body.

It is, therefore, the prime object of the present invention to provide a clamping system for sealingly connecting specially configured coupling members of a two piece ostomy device.

It is another object to provide a clamping system for a two piece ostomy device wherein trauma to the patient is eliminated.

It is another object of the present invention to provide a clamping system for two piece ostomy device wherein no force is applied to the patient as the clamp is mounted or removed.

It is another object of the present invention to provide a clamping system for a two piece ostomy device in which a clasp type locking system, connected by the living hinge, is employed.

It is another object of the present invention to provide a clamping system for two piece ostomy device wherein a pin and slot locking system is employed.

It is another object of the present invention to provide a clamping system for a two piece ostomy device wherein a serrated clasp locking system is employed.

It is another object of the present invention to provide a clamping system for a two piece ostomy device wherein a change purse type locking system is employed.

It is another object of the present invention to provide a clamping system for a two piece ostomy device which may be adapted for use with a pouch having a conventionally configured coupling member.

In accordance with one aspect of the present invention, a clamping member is provided for use in a two piece ostomy device. The clamping member is adapted to sealingly connect the coupling members of an adhesive body mounting means and a collection receptacle means, respectively. Each of the coupling members includes a substantially upstanding wall having a substantially outwardly extending projection. The clamping member has a recess adapted to receive the projections. Means are also provided for locking the clamping member in a position with the projections received in the recess.

Preferably, the coupling members are in the form of rigid plastic rings which include an axially extending wall. The projections on the coupling members are radially extending and substantially annular. The recess in the clamping member is also substantially annular.

Preferably, the projections are each provided with a camming surface. The camming surfaces on the projections are oppositely inclined. The recess is defined by oppositely inclined sides. Preferably, the recess has substantially "V" cross sectional configuration. The camming surfaces of the projections cooperate with the inclined surfaces of the recess to draw the members toward each other as the clamp is locked.

In one preferred embodiment, the locking means includes clasp means in the form of a toggle clasp. The clasp includes a first hook means mounted on one section of the member, and lever arm means movably mounted on the other section of the member. Second hook means are mounted on the lever arm means. The lever arm means is movable between a first position, wherein the first and second hook means engage and the member sections are spaced from each other, and a second position, where the member sections are substantially abutting.

The lever arm means is mounted on the second section by lever arm means support means. Means are provided for hingeably connecting the lever arm means to lever arm means support means. Further, means are provided for hingeably mounting the second hook means on the lever arm means. Means are provided for retaining the lever arm in the second position.

In a second preferred embodiment, the locking means comprises a protrusion and a recess. The protrusion is frictionally engaged within the recess to lock the clasp. The protrusion and recess are each mounted on substantially radially extending parts of the member sections, respectively.

In a third preferred embodiment, the locking means comprises serrated clasp means. The serrated clasp means includes a first part mounted on one section of the annular member. The first part has a serrated surface facing in the first direction. A second part, mounted on the other section of the member, has a serrated surface facing in a direction substantially opposite to the first direction.

In another preferred embodiment, the locking means comprises change purse type clasp means. These locking means include first means mounted on one section of the member. The first means includes a neck portion offset in a first direction from the radial center line of the member. A second means is mounted on the other section of the member. It includes a neck portion offset in the second direction from the radial center line. The first and second means are movable relative to each other such that the neck sections engage.

In another embodiment of the present invention, the member is divided into first and second substantially semi-circular sections. One of the sections is integral with or permanently affixed to one of the coupling members. Specifically, the member has a semi-circular section which is molded integrally as a part of the coupling member. The coupling member has a ring like configuration.

In accordance with another aspect of the present invention, an ostomy device is provided including adhesive body mounting means having a coupling ring and collection receptacle means having a coupling ring. Clamping means are provided for sealingly connecting the coupling rings. Each of the coupling rings includes a substantially axially extending wall with a substantially radially extending annular projection. The clamping means includes a substantially annular clamping member adapted to substantially surround the rings and having a recess adapted to receive the projections and means for locking the clamping means in position surrounding the coupling rings.

Preferably, each of the projections has a camming surface. The camming surfaces are inclined in opposite directions such that the coupling rings cooperate to form a projection with a substantially "V"-shaped cross sectional configuration.

The recess in the annular member has oppositely oriented inclined surfaces. The coupling rings are drawn towards each other as the locking means are actuated.

In accordance with another aspect of the present invention, an ostomy device is provided comprising adhesive body mounting means having a coupling member and collection receptacle means having a coupling member. Adapter means affixable to one of the coupling members is provided. Means are provided for sealingly connecting the adapter and the other coupling member. The adapter and the other coupling member each include a substantially upstanding wall having a substantially outwardly extending projection. The connecting means includes a clamping member having a recess adapted to receive the projections. Means are provided for locking the clamping member in position surrounding the other coupling ring and the adapter with said projections in said recess. Means are provided to affix the adapter on the one coupling member. The affixing means comprises first and second inter-engaging means on the adapter and the one coupling member, respectively.

To these and such other objects which may hereinafter appear, the present invention relates to a clamping system for a two piece device as described in the following specification and recited in the annexed claims, taken together with the accompanying drawings wherein like numerals refer to like parts and in which:

FIG. 2 is an enlarged cross sectional view showing the clamping member and coupling rings of FIG. 1 in aligned position, prior to locking;

FIG. 3 is a view similar to FIG. 2, but showing the clamping member in the locked position with respect to the rings;

FIG. 5 is a view similar to FIG. 4, but showing the clasp in the locked position;

FIG. 6 is a perspective view of the clamping member of the present invention, illustrating how it can be used with a pouch having a conventional coupling ring and an adapter;

FIG. 9 is an elevational view of a serrated clasp type locking member of the present invention;

FIG. 10 is a view similar to FIG. 9, but showing the clasp in the locked position;

FIG. 11 is an elevational view of a pin and socket type locking member of the present invention in the unlocked position;

FIG. 12 is a top view of the pin and socket type clasp of FIG. 11 showing the clasp locked;

FIG. 13 is a side view of the pin and socket type clasp of FIG. 11 in the locked position;

FIG. 14 is a view taken along line 14—14 of FIG. 12;

FIG. 15 shows a change purse type clasp of the present invention in its opened condition;

FIG. 16 is a top view of the change purse type clasp of FIG. 15;

FIG. 17 is a side view of the change purse type clasp of FIG. 15;

FIG. 18 is a view taken along line 18—18 of FIG. 16;

FIG. 19 is a plan view of another preferred embodiment of the present invention in which the clamp is integral with the rings showing the clamps in the open position;

FIG. 20 is a view similar to FIG. 19 but showing the clamp in the closed position;

Figure 1:
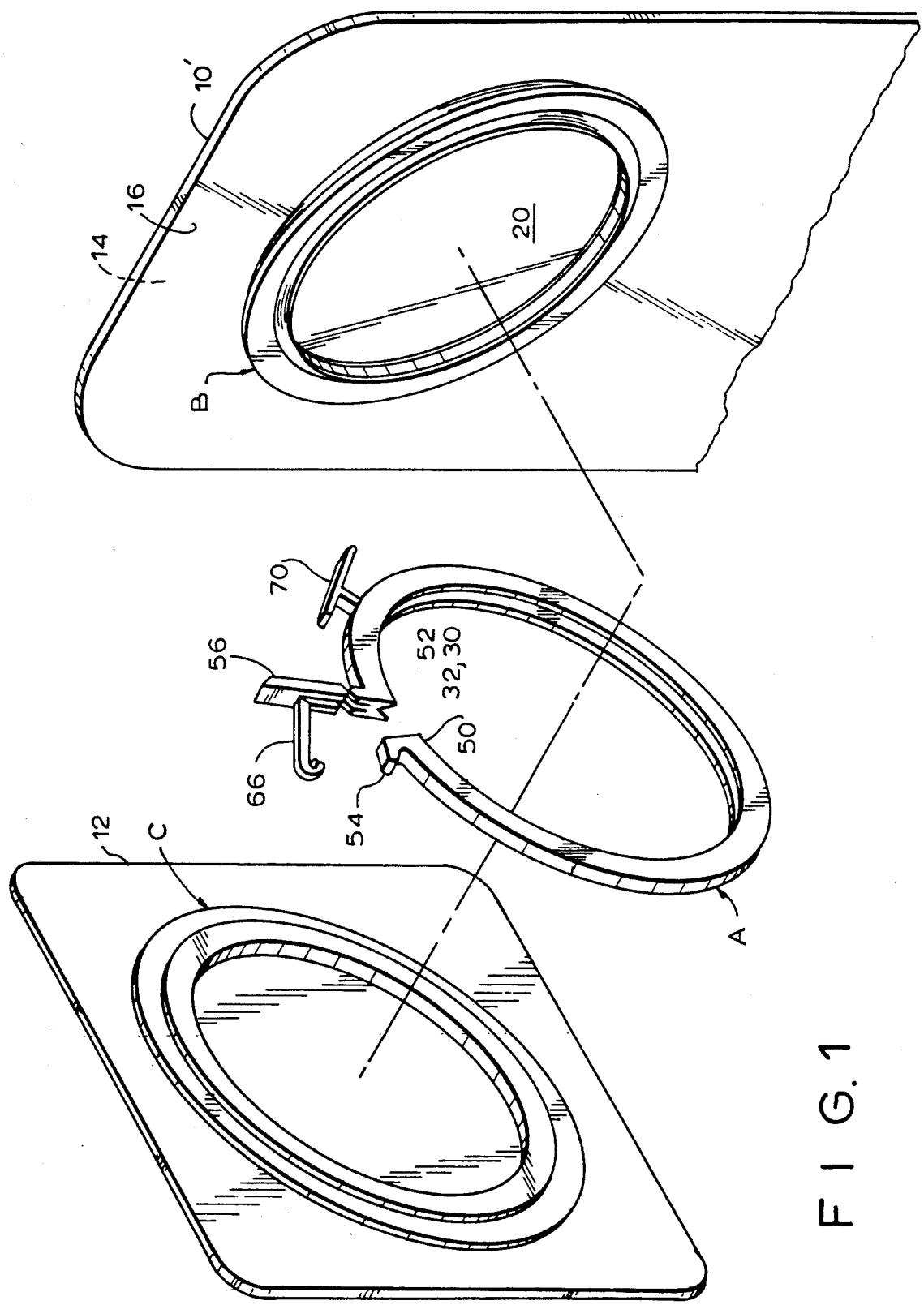
FIG. 1 is a perspective view of the clamping member of the present invention and a specially designed ostomy device with which it is used.

As seen in the figures, with particular reference to FIG. 1, the present invention relates to a clamping member, generally designated A, which preferably takes the form of a generally circular plastic ring which is severed at one point. Clamp A is composed of plastic which is flexible enough such that the ends of the clamp can be displaced with respect to each other a short distance to increase the inner diameter of the clamp. In its opened or enlarged condition, clamp A can be fitted around specially designed coupling rings, generally designated B and C, mounted on a conventional two piece ostomy pouch 10 and adhesive faceplate or dressing 12, respectively.

As best seen in FIG. 2, pouch 10, shown in cross section at the right, includes an exterior wall 14 and an interior wall 16 made of thin plastic film. The walls are heat welded at the periphery 18 to form a pouch which may be opened or closed at the bottom, depending upon the intended application. Wall 16 has an opening 20 adapted to receive the stoma which is defined by coupling ring B. Ring B includes a substantially upstanding or axially extending wall 22. Wall 22 has a projection 24 which extends outwardly or radially. At the lower left hand corner of wall 22 is a sealing rim 26, the purpose of which is best visualized in FIG. 3, which shows clamp A in the locked position.

The exterior surface of wall 22 is provided with an inclined camming surface 28. Surface 28 is designed to cooperate with a similarly inclined surface 30, which defines a portion of the recess on the interior of clamp A. The other portion of the recess in clamp A is defined by a surface 32 which is inclined in a direction substantially opposite to the incline of surface 30, that is, surfaces 30 and 32 are substantially perpendicular to each other forming a V-shaped annular notch along the interior of clamp A.

Surface 32 of clamp A is designed to cooperate with correspondingly inclined camming surface 34 on ring C. Ring C is essentially the mirror image of ring B without sealing rim 26. Ring C includes an upstanding, axially extending wall 36 and a outwardly extending radial projection 38. Upstanding wall 36 is mounted on a base 39 which, in turn, is welded or adhesively attached to the surface of faceplate 12.

As will best be appreciated by a comparison of FIGS. 2 and 3, as clamp A is tightened around rings B and C, surface 28 cooperates with surface 30, and surface 34 cooperates with surface 32 to draw the rings B and C toward each other such that sealing rim 26 abutts firmly against the lower right hand corner of ring C. Thus, any space between the rings is completely sealed eliminating any possibility of gaseous or semi-solid waste escaping.

Figure 8:
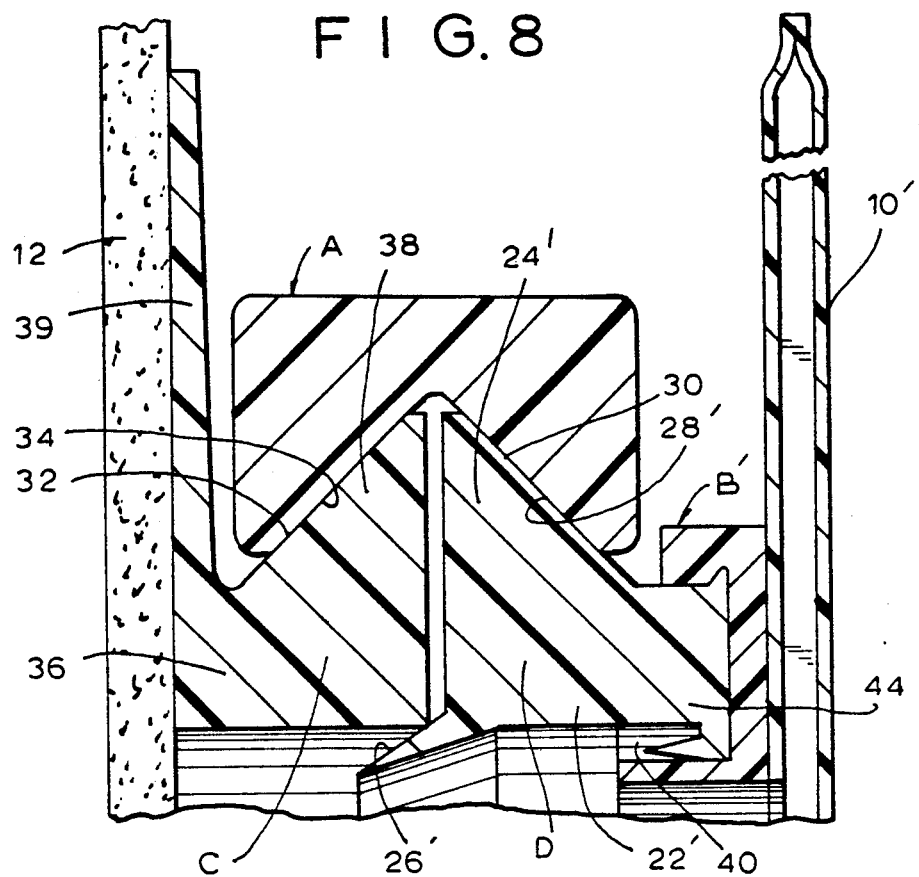
FIG. 8 is a view similar to FIG. 7, but showing the clamping member in its locked position.
Figure 7:
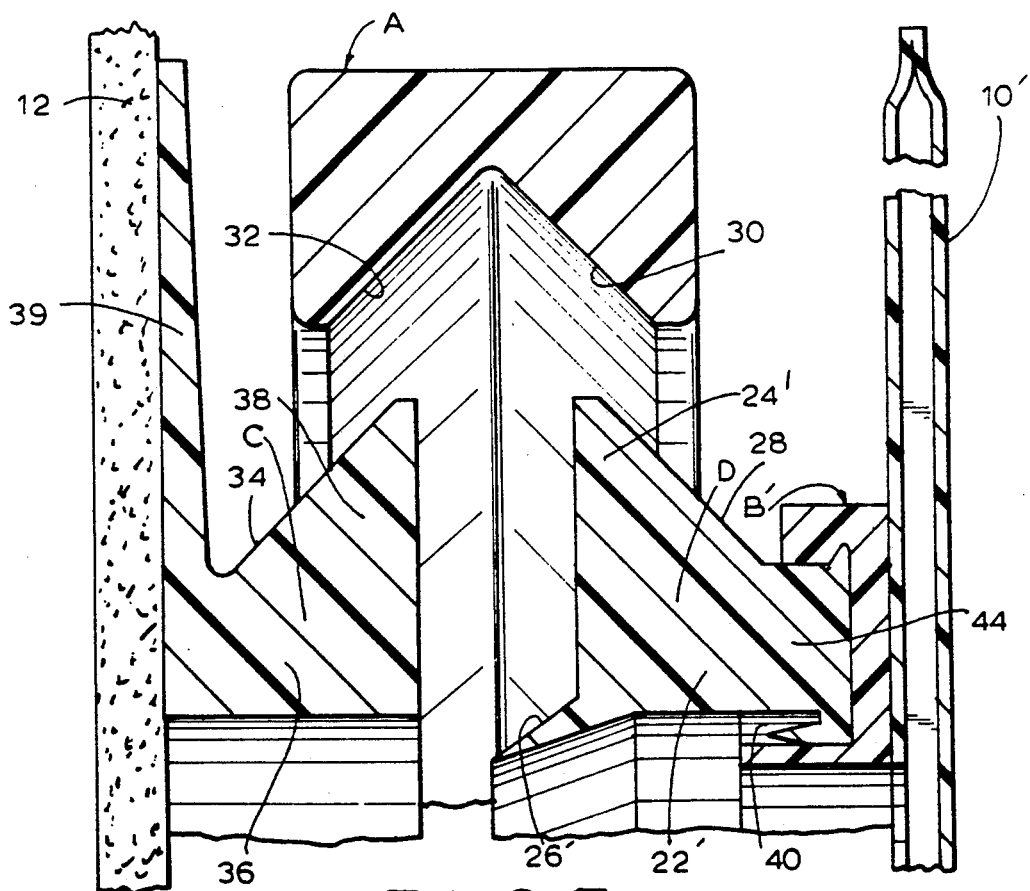
FIG. 7 is an enlarged cross sectional view of the clamping member, adapter and coupling rings of FIG. 6 with the parts aligned but not locked.

Referring now to FIGS. 6, 7 and 8, these figures illustrate the use of clamp A with the same specially designed faceplate ring C and a conventional ostomy pouch 10' having a conventional channel shaped coupling ring B'. In this case, an adapter, generally designated D, is required. Adapter D is affixed to coupling ring B' so as to provide a configuration which is functionally equivalent to specially designed coupling ring B.

Adapter D has the essentially same operative structure as ring B in the first embodiment, including wall 22', projection 24' rim 26' and surface 28'. However, adapter D has a portion adapted to connect with the coupling ring on the pouch. Conventional pouch 10' has a conventionally shaped coupling ring B' which includes a recess 40. Adapter D has a protrusion 44 extending outwardly, designed to be removably retained within recess 40. The structure shown herein is essentially that disclosed in Steer et al., U.S. Pat. No. 4,460,363, entitled OSTOMY BAG. However, the configuration of the inter-engaging parts between adapter D and ring B' is shown here by way of example and other configurations may function in this regard as well.

It will now be appreciated, by a comparison of FIGS. 6 and 7, that when once adapter D is engaged to coupling ring B', clamp A of the present invention operates exactly the same way with adapter D as it does in the embodiment shown in FIGS. 1, 2 and 3.

Whether or not clamp A is used with an adapter after it is in position surrounding the coupling rings, it is tightened and locked. The locking means can take one of several different preferred forms, as illustrated in FIGS. 4 through 18.

Figure 4:
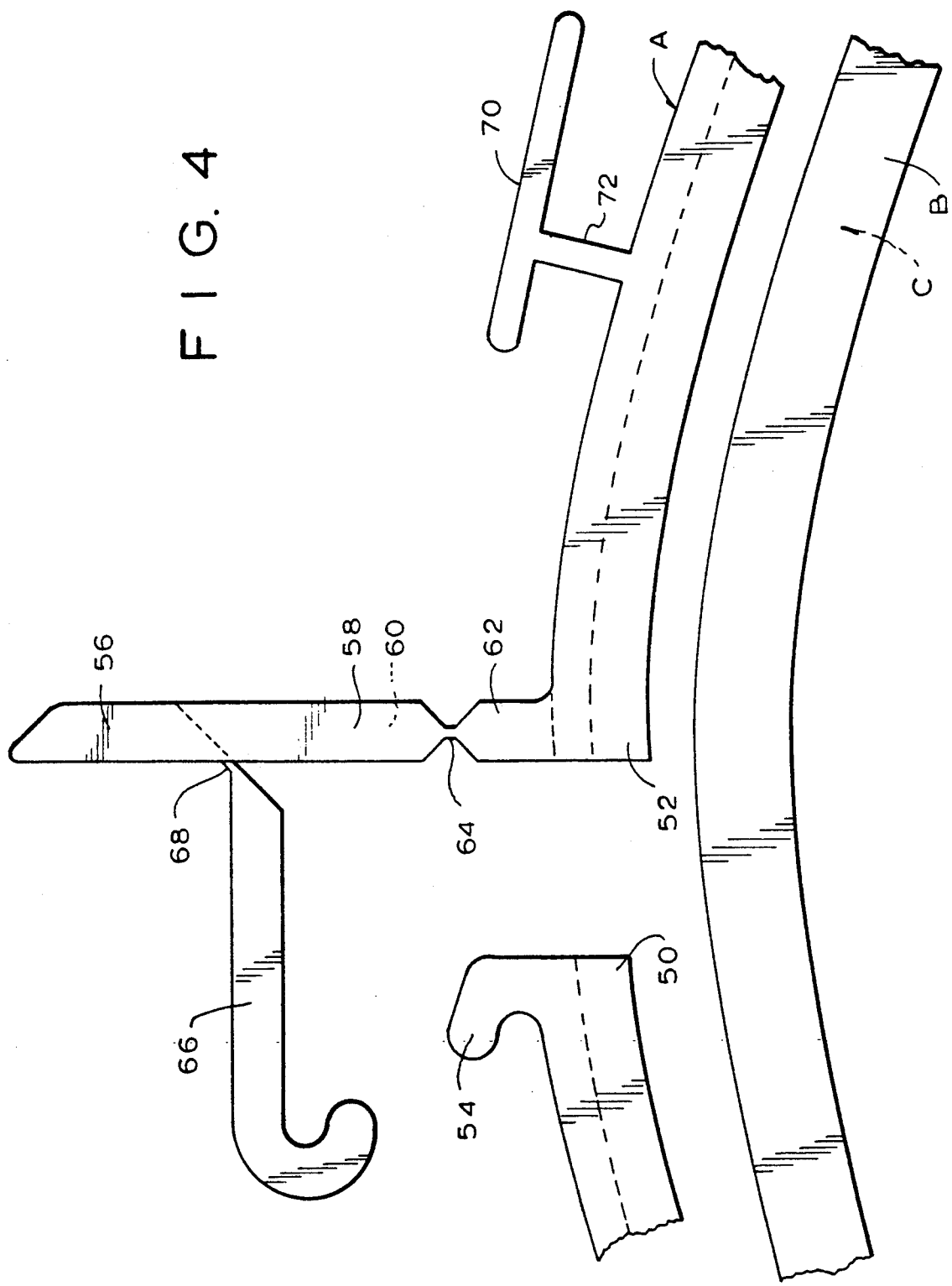
FIG. 4 is an enlarged plan view of the toggle clasp portion of the present invention in the unlocked position.

The first preferred form of the locking means, which is a toggle-type clasp, is illustrated in FIGS. 4 and 5. As seen in FIG. 4, clamp A has two end sections 50 and 52. On end section 50 is provided an integrally molded hook 54 extending outwardly thereof. On end 52 is a lever arm 56 which has a bifuricated lower portion, including legs 58 and 60, connected to an outwardly extending protrusion 62 by a living hinge 64.

Connected to the mid section of lever arm 56 is a second hook member 66. Hook member 66 is connected to lever arm 56 by a second living hinge 68.

Spaced along the surface of clamp A is a radially extending protrusion 72 and a circumferentially extending member 70 forming a substantially T-shaped catch. Protrusion 72 of the T-shaped catch is flexible to permit the top of member 30 to be moved relative to the surface of clamp A.

As seen in FIG. 5, ends 50 and 52 can be brought together, thereby sealing coupling rings B and C together, by engaging hooks 66 and 54 and pressing the outward portion of lever 56 such that it rotates clockwise around living hinge 64. As the outward tip of lever arm 56 moves toward the surface of clamp A, the T-shaped catch is rotated in a clockwise direction by applying a force at end 74 of member 70 so as to permit the tip of lever arm 56 to be situated beneath the other end of member 70, as shown in phantom in FIG. 5. End 74 is then released, causing member 70 to return to its original position, as shown in solid in FIG. 5, hence maintaining lever arm 56 in the locked position. In order to open the locking means, end 74 of member 70 is again depressed, lever arm 56 is rotated counterclockwise and hook 54 is released from hook 66.

It should be appreciated that the locking and unlocking procedures require only forces applied to lever arm 56 and the T-shaped catch and only in a radial direction with respect to rings B and C. No force is directed towards the patient's body.

A second preferred embodiment of the locking means is illustrated in FIGS. 9 and 10, which illustrate a serrated type clasp. The serrated type clasp includes an outwardly facing surface 80 on end 50 of clamp A provided with a serrated edge and a similar but oppositely facing surface 82 with a corresponding serrated edge provided on an elongated portion extending from end section 52. The serrated edges are oppositely contoured so as to inter-engage as illustrated in FIG. 10. The serrated edges are provided with camming portions as is customary in this type of clasp, such that substantially radially extending grip surfaces 84 and 86 can be held between the thumb and forefinger. As the thumb and forefinger are brought together, the clasp portions slide with respect to each other until they rest in the locked position as shown in FIG. 10.

Here, again, it should be appreciated that the clasp can be locked without exerting any force on a patient. Similarly, the clasp is unlocked by pulling the elongated portion of end section 52 radially outwardly to disengage the surfaces 80 and 82.

FIGS. 11 through 14 illustrate another preferred embodiment of the locking means in the form of a pin and socket arrangement. In this case, end 50 of clamp A is provided with a radially extending element 90, with a circular opening 92 in its mid section.

End 52 of clamp A is also provided with a generally radially extending element 94. Extending from the surface of element 94 is a protrusion 96 designed to be frictionally engaged within opening 92 in element 90 and to extend beyond the surface of the element. Protrusion 96 has a lower portion with a generally conical shape which tends to cause elements 90 and 94 to draw together as it is inserted into opening 92 and to hold the elements 90 and 94 adjacent, as shown in FIGS. 12 and 13. It should also be appreciated that opening of elements 90 and 94 is easily accomplished by pushing on the upper, exposed portion of protrusion 96. FIG. 14 illustrates that rings B and C are forced to abut as elements 92 and 94 are brought towards each other and maintained in abutting position by the shape of protrusion 96.

The pin and socket locking arrangement, like the previous arrangements, requires only radially directed locking and unlocking forces. No force is directed toward the patient.

FIGS. 15 through 18 illustrate another preferred form of the locking means of the present invention which, in this case, takes the form of a change purse type clasp. In particular, ends 50 and 52 of clamping member A are now provided with generally radially extending elements 100 and 102, each of which is offset from the plane passing through the middle of clamp A, perpendicular to its axes, such that they can twist around each other, as illustrated in FIGS. 16 and 17, thereby locking ends 50 and 52 together and sealing rings B and C as shown in FIG. 18. Here again, no force is exerted on the patient as the clamp is locked or unlocked.

Figure 21:
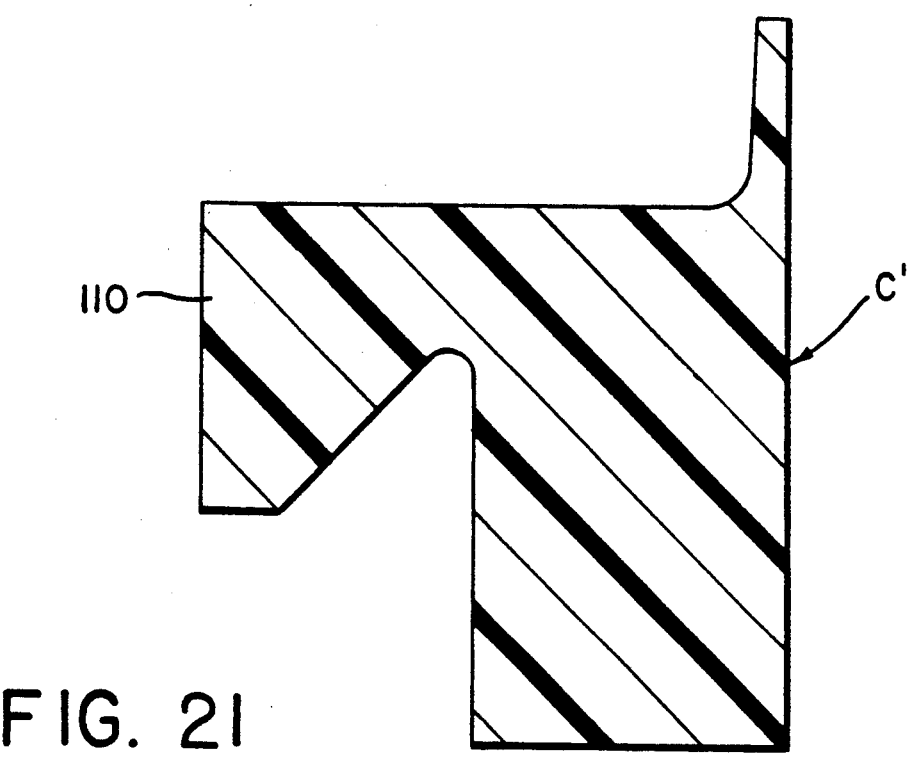
FIG. 21 is a cross sectional view taken along line 21—21 of FIG. 20.
Figure 22:
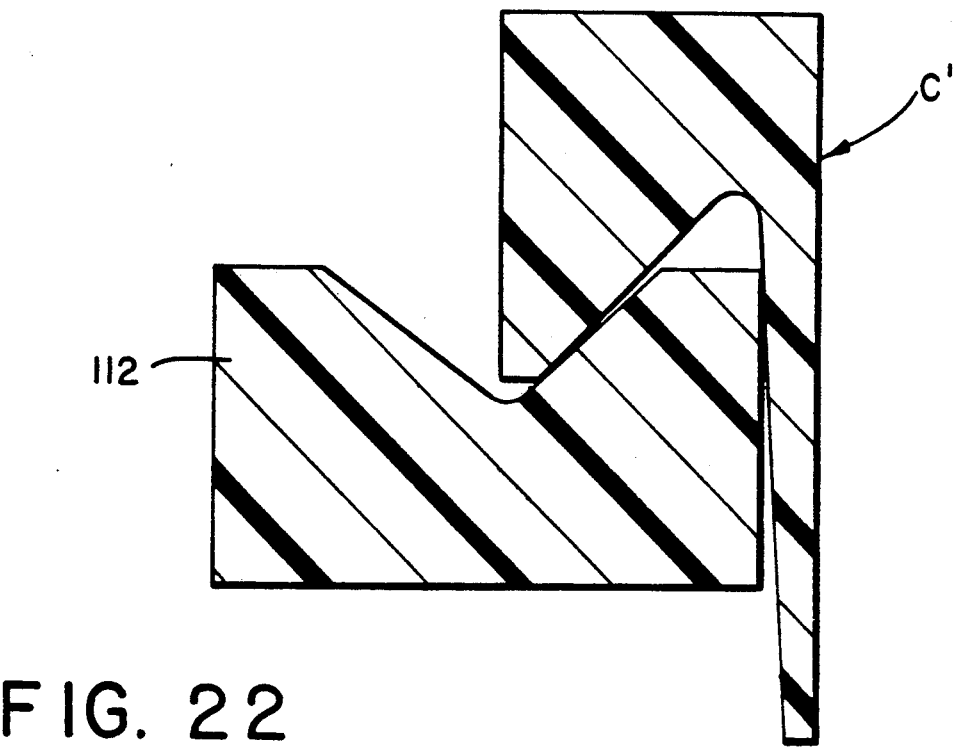
FIG. 22 is a cross sectional view taken along line 22—22 of FIG. 20.

FIGS. 19 through 22 illustrate a slightly modified version of clamp A in the form of clamp A', which is divided into two half sections 110 and 112. Sections 110 and 112 are connected together by a living hinge 114. Section 110 is affixed to or preferably integral with a faceplate coupling ring C'. FIG. 20 shows clamp A' in the locked position. FIGS. 21 and 22, respectively, show the cross sectional shape of sections 110 and 112. Clamp A' operates exactly the same as clamp A, except that it is pre-positioned with respect to the faceplate coupling ring.

It will now be appreciated that the present invention relates to a clamping member designed for use with a two piece ostomy device. In one embodiment, the clamping member cooperates with specially configured coupling rings to surround and sealingly connect the rings. In a second embodiment, an adapter is used with a conventionally structured pouch coupling ring. In both embodiments mounting of the clamp is accomplished in a manner which does not require the application of any force to the body of the patient. The clamping member is generally circular in structure and includes an internal recess which has surfaces which cooperate with the surfaces on the coupling rings to draw the rings towards each other as the clamp is tightened by the locking means. The locking means can take one of several forms, including a toggle clasp connecting by a living hinge, a pin-and-socket arrangement, a serrated clasp or a change purse type clasp.

While only a limited number of preferred embodiments have been disclosed herein for purposes of illustration, it is obvious that many variations and modifications can be made thereto. It is intended to cover all of these variations and modifications which fall within the scope of the present invention as defined by the following claims:

I claim:

1. For use with a two piece ostomy device of the type including adhesive body mounting means with a coupling member and waste collection means with a coupling member, each of the coupling members comprising a substantially upstanding wall with a substantially outwardly extending projection, means for sealingly connecting the coupling members, said connecting means comprising a clamping member having a recess adapted to receive the projections therein, said clamping member being divided into first and second sections, one of said first and second sections being permanently affixed to one of said coupling members and means for locking said clamping member in a position wherein said projections are received in said recess in said other of said first and second clamping member sections.

2. The connecting means of claim 1 wherein said recess is substantially annular.

3. The connecting means of claim 1 wherein said recess is defined by substantially oppositely inclined surfaces.

4. The connecting means of claim 3 wherein the projections include camming surfaces and where said inclined surfaces of said recess cooperate with the camming surfaces to draw the coupling members toward each other as said clamping member is locked.

5. The connecting means of claim 1 wherein said recess has a substantially "V"-shaped cross sectional configuration.

6. The connecting means of claim 1 wherein said locking means comprises clasp means.

7. The connecting means of claim 6 wherein said clasp means comprises a toggle clasp.

8. The connecting means of claim 1 wherein said clamping member comprises first and second end sections and wherein said locking means comprises first hook means mounted on said first end section, lever arm means movably mounted on said second end section, second hook means mounted on said lever arm means, said lever arm means being movable between a first position, where said first and second hook means engage and said end sections are spaced relative to each other and a second position where said end sections are proximate each other.

9. The connecting means of claim 8 further comprising lever arm means support means mounted on said second end section and means for hingeably connecting said lever arm means to said lever arm means support means.

10. The connecting means of claim 8 further comprising means for hingeably mounting said second hook means on said lever arm means.

11. The connecting means of claim 1 further comprising means for hingeably connecting said first and said second clamping member sections.

12. A two piece ostomy device comprising adhesive body mounting means having a coupling ring, waste collection means having a coupling ring and means for sealingly connecting said coupling rings, each of said coupling rings comprising a substantially axially extending wall having a substantially radially extending projection, said connecting means having a recess adapted to receive said projections and being divided into first and second sections, one of said first and second sections being permanently affixed to one of said coupling rings and means for locking said clamping member in a position wherein said projections are received in said recess in said other of said first and second sections of said connecting means.

13. The connecting means of claim 12 wherein said recess is defined by substantially oppositely inclined sides.

14. The connecting means of claim 12 wherein said recess has a substantially "V"-shaped cross sectional configuration.

15. The connecting means of claim 12 wherein said projections comprise substantially oppositely inclined camming surfaces.

16. The connecting means of claim 13 wherein said projections comprise oppositely inclined camming surfaces.

17. The connecting means of claim 16 wherein said camming surfaces on said projections cooperate with said inclined surfaces of said recess to draw said members toward each other as said clamping member is locked.

18. The connecting means of claim 12 wherein said locking means comprises clasp means.

19. The connecting means of claim 18 wherein said clasp means comprises a toggle clasp.

20. The connecting means of claim 12 wherein said clamping member comprises first and second end sections and wherein said locking means comprises first hook means mounted on said first end section, lever arm means movably mounted on said second end section, second hook means mounted on said lever arm means, said lever arm means being movable between a first position, where said first and second hook means engage and said end sections are spaced from each other and a second position where said end sections are substantially abutting.

21. The connecting means of claim 20 further comprising lever arm means support means mounted on said second end section and means for hingeably connecting said lever arm means to said lever arm means support means.

22. The connecting means of claim 20 further comprising means for hingeably mounting said second hook means on said lever arm means.

23. The connecting means of claim 12 further comprising means for hingeably connecting said first and said second clamping member sections.

* * * * *